United States Patent
Joo et al.

(10) Patent No.: US 10,750,965 B2
(45) Date of Patent: Aug. 25, 2020

(54) METHOD FOR DETECTING DISEASE USING HIGH RESOLUTION MANOMETRY, AND APPARATUS THEREOF

(71) Applicant: UNIVERSITY OF ULSAN FOUNDATION FOR INDUSTRY COOPERATION, Ulsan (KR)

(72) Inventors: Se Gyeong Joo, Seoul (KR); Kee Wook Jung, Seoul (KR); Seung Jae Myung, Seoul (KR); Hwoon Yong Jung, Seoul (KR)

(73) Assignee: UNIVERSITY OF ULSAN FOUNDATION FOR INDUSTRY COOPERATION, Ulsan (KR)

( * ) Notice: Subject to any disclaimer, the term of this patent is extended or adjusted under 35 U.S.C. 154(b) by 1009 days.

(21) Appl. No.: 15/310,793

(22) PCT Filed: Mar. 20, 2015

(86) PCT No.: PCT/KR2015/002761
§ 371 (c)(1),
(2) Date: Nov. 14, 2016

(87) PCT Pub. No.: WO2015/142120
PCT Pub. Date: Sep. 24, 2015

(65) Prior Publication Data
US 2017/0119267 A1 May 4, 2017

(30) Foreign Application Priority Data
Mar. 21, 2014 (KR) .................. 10-2014-0033402
Mar. 21, 2014 (KR) .................. 10-2014-0033403

(51) Int. Cl.
*A61B 5/03* (2006.01)
*A61B 5/00* (2006.01)
(Continued)

(52) U.S. Cl.
CPC ............ *A61B 5/037* (2013.01); *A61B 5/0538* (2013.01); *A61B 5/227* (2013.01); *A61B 5/4233* (2013.01);
(Continued)

(58) Field of Classification Search
CPC ....... A61B 5/037; A61B 5/045; A61B 5/4255; A61B 5/6832; A61B 5/6833;
(Continued)

(56) References Cited

U.S. PATENT DOCUMENTS

2009/0024001 A1   1/2009   Parks et al.
2013/0158365 A1   6/2013   Chey et al.

FOREIGN PATENT DOCUMENTS

KR   10-2002-0093860 A   12/2002
KR      10-0816847 B1    3/2008

OTHER PUBLICATIONS

International Search Report for PCT/KR2015/002761 dated Jun. 17, 2015 from Korean Intellectual Property Office.

*Primary Examiner* — Eun Hwa Kim
(74) *Attorney, Agent, or Firm* — Revolution IP, PLLC

(57) ABSTRACT

A method for detecting disease using a manometry includes obtaining pressure values from each of the plurality of pressure sensors during a pre-set time, obtaining a three-dimensional pressure distribution showing the changes in the pressure values according to location and time by using the time, the pressure values, and locations in which the pressure sensors are disposed within the arbitrary location section, and calculating the volume integral value of the interest location which is predetermined in accordance with the disease, in the three-dimensional pressure distribution.

5 Claims, 10 Drawing Sheets

(51) Int. Cl.
*A61B 5/22* (2006.01)
*A61B 5/053* (2006.01)

(52) U.S. Cl.
CPC .......... *A61B 5/4255* (2013.01); *A61B 5/6853* (2013.01); *A61B 5/6873* (2013.01); *A61B 5/7282* (2013.01); *A61B 5/748* (2013.01); *A61B 5/4222* (2013.01); *A61B 5/6867* (2013.01); *A61B 2562/0209* (2013.01); *A61B 2562/0247* (2013.01); *A61B 2562/043* (2013.01); *A61B 2562/063* (2013.01)

(58) Field of Classification Search
CPC ... A61B 5/6846; A61B 5/6852; A61B 5/6853; A61B 5/6873
See application file for complete search history.

[Figure 1]
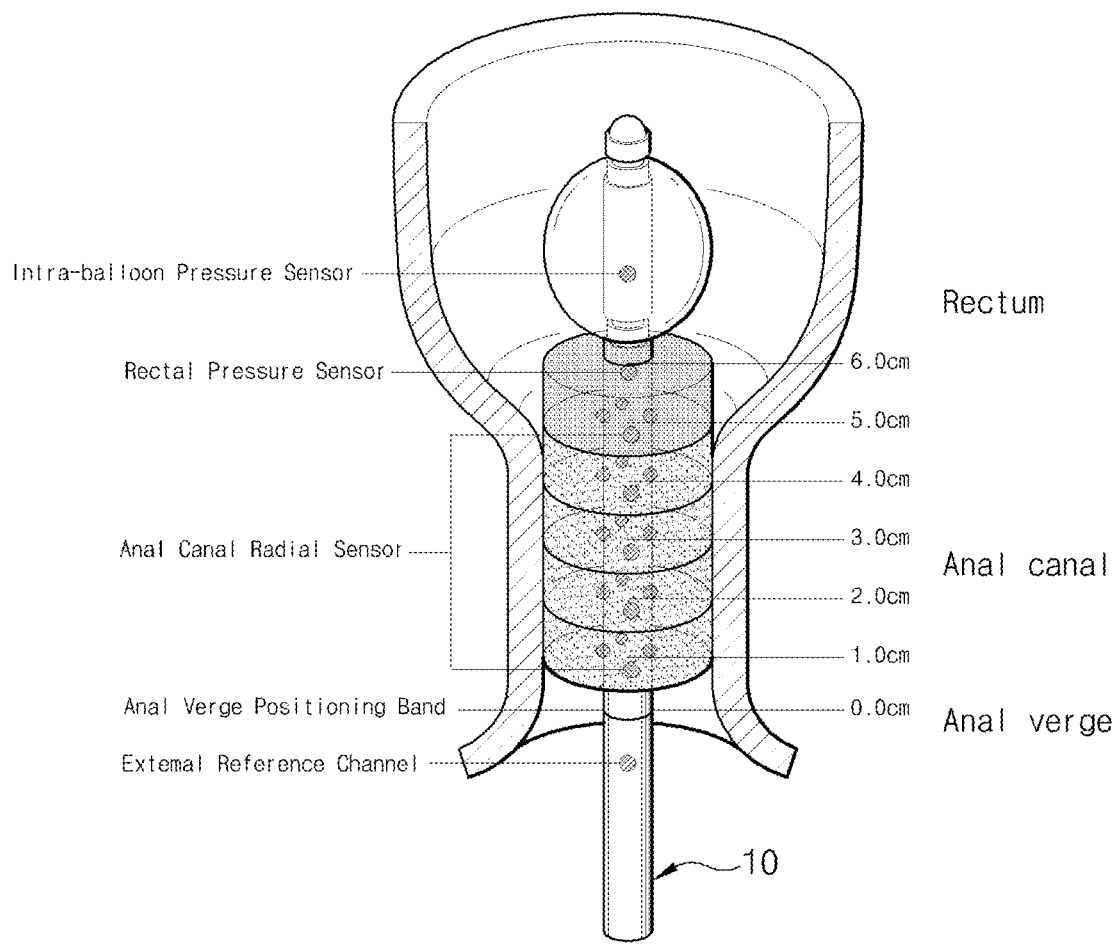

[Figure 2]
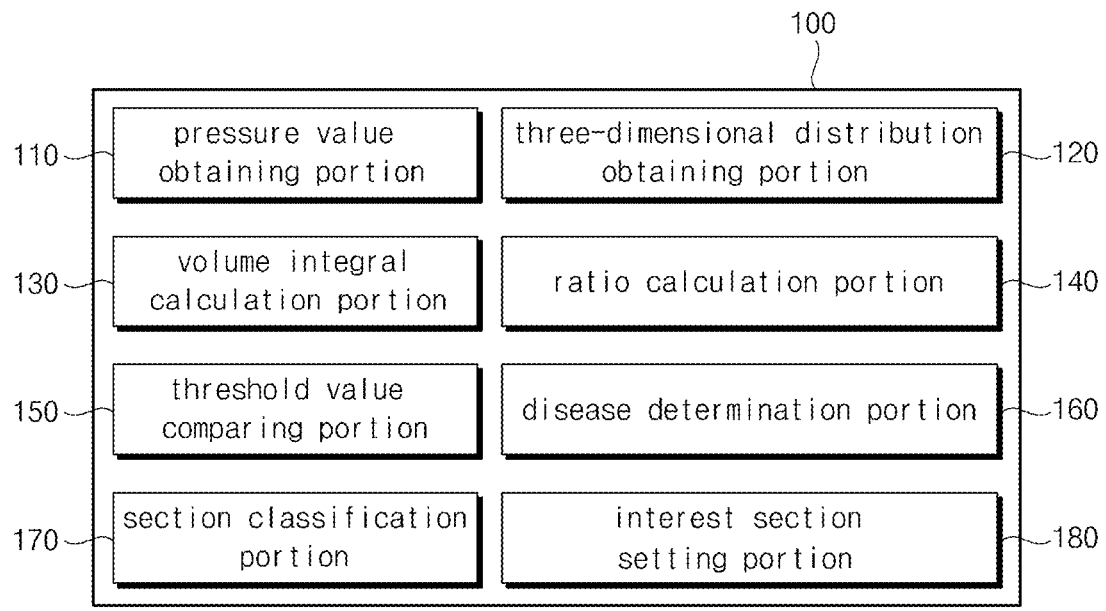
[Figure 3]
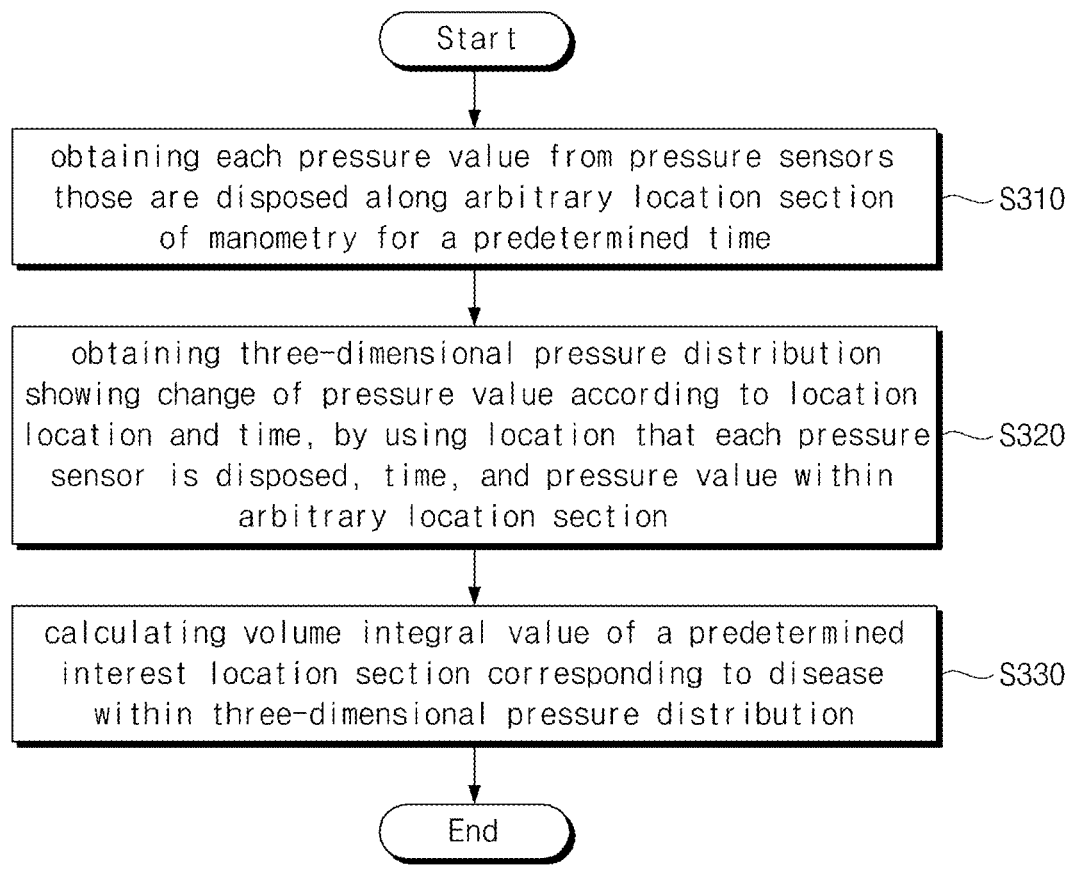

[Figure 4]
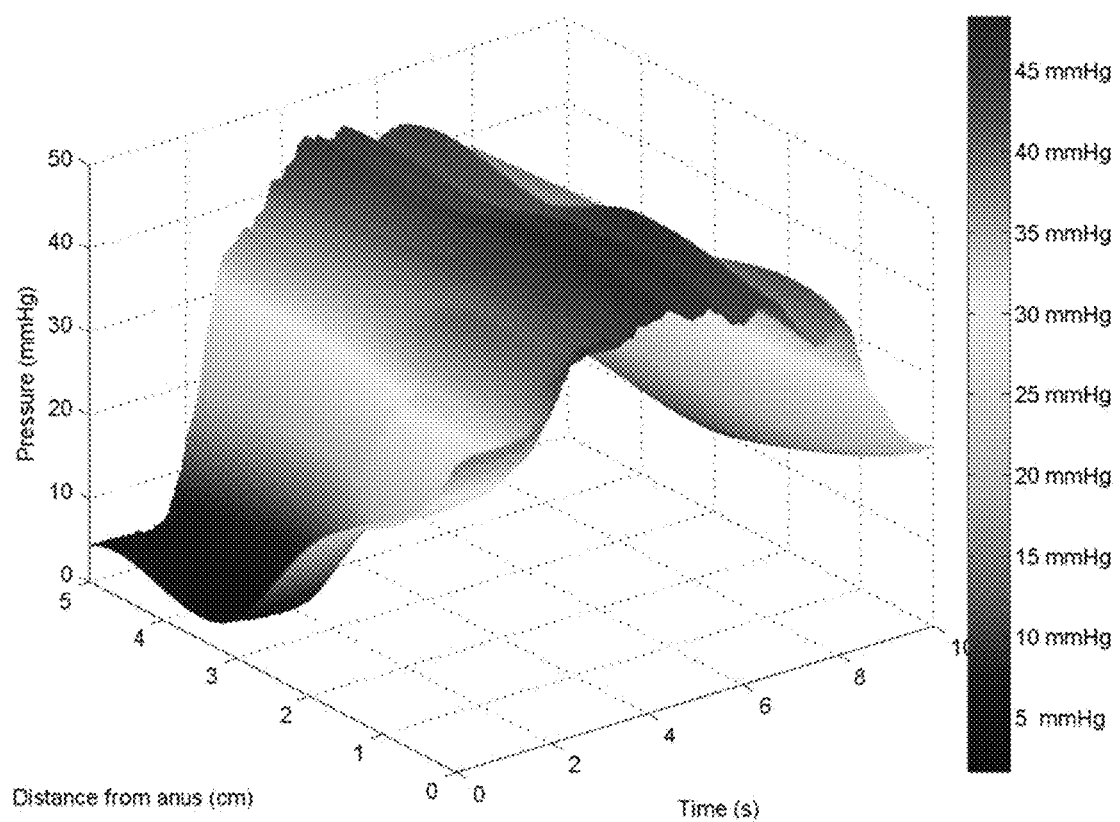

[Figure 5]
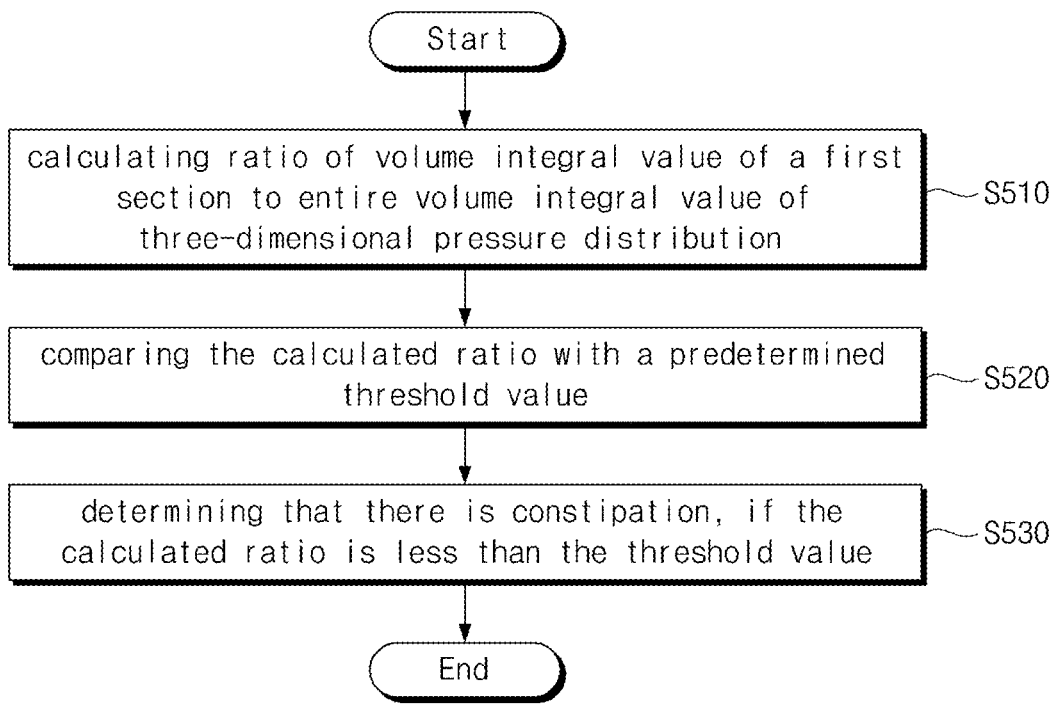
[Figure 6]
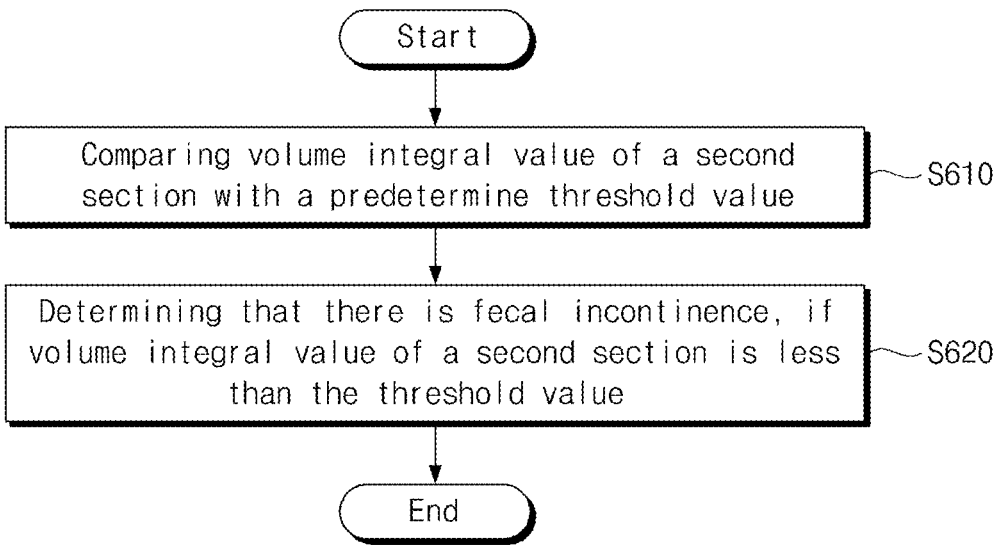

【Figure 7】
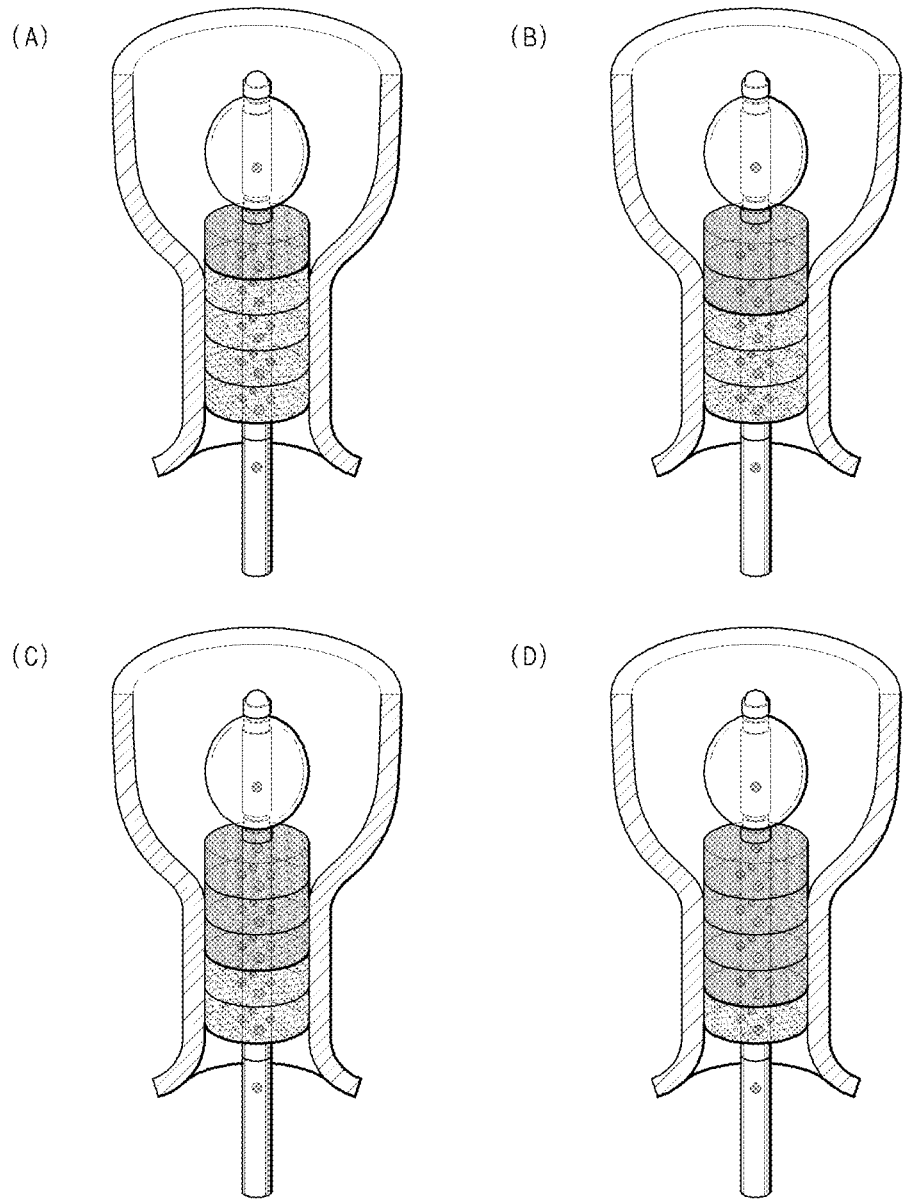

【Figure 8】
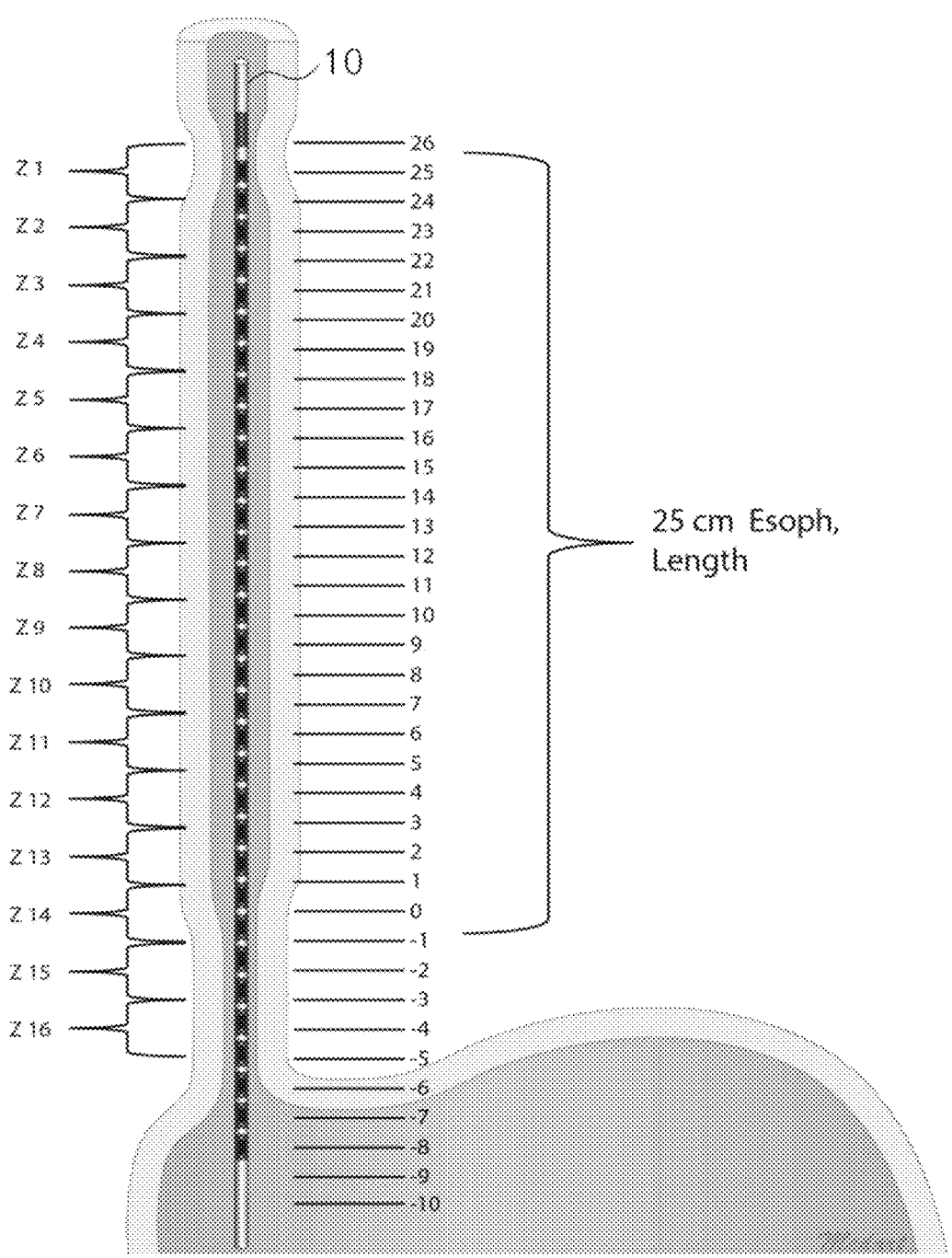

[Figure 9]
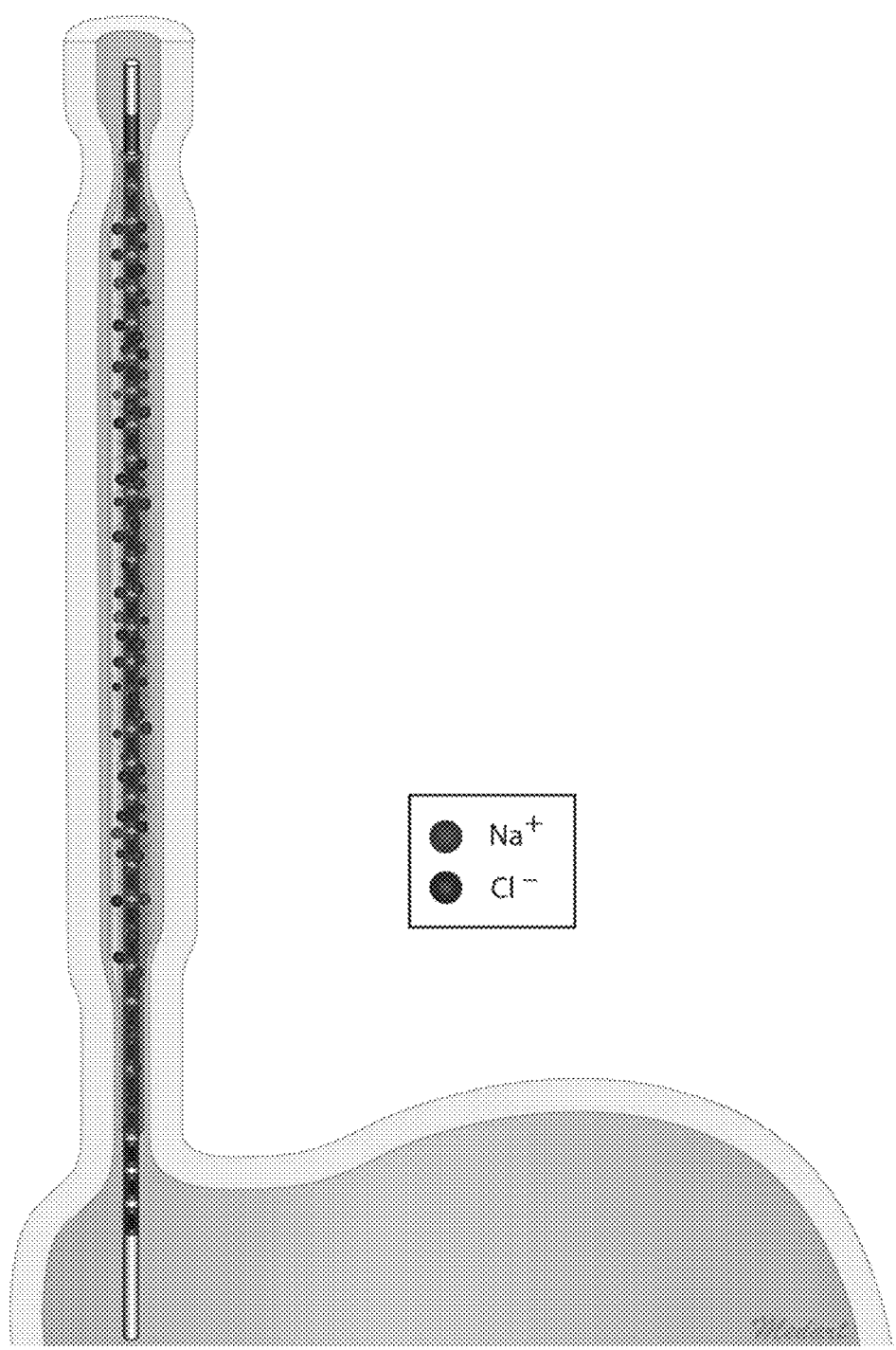

[Figure 10]
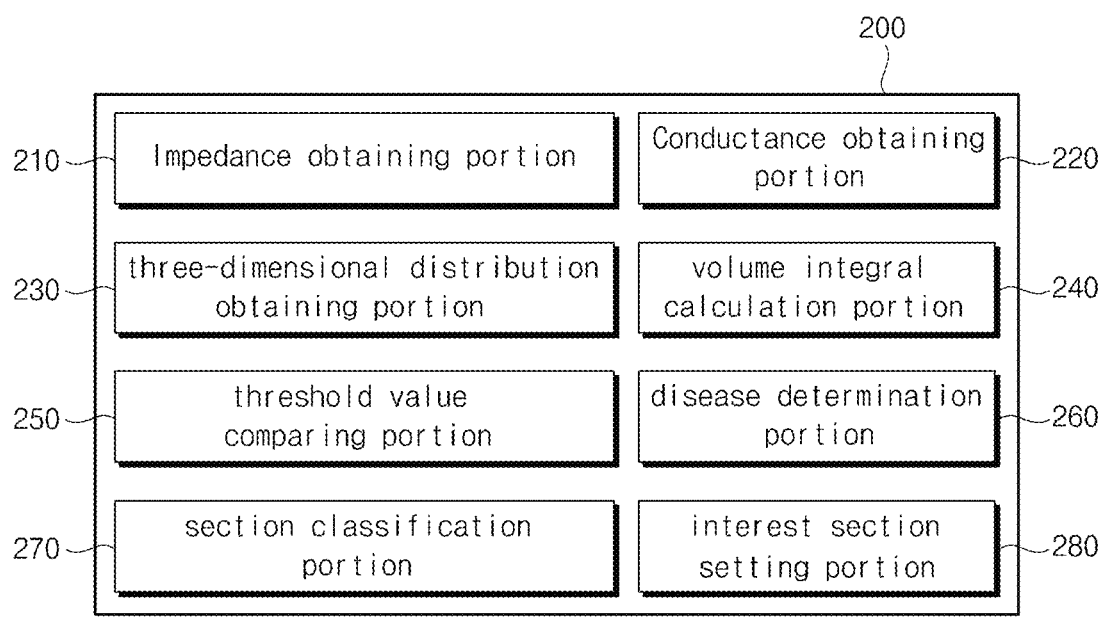

[Figure 11]
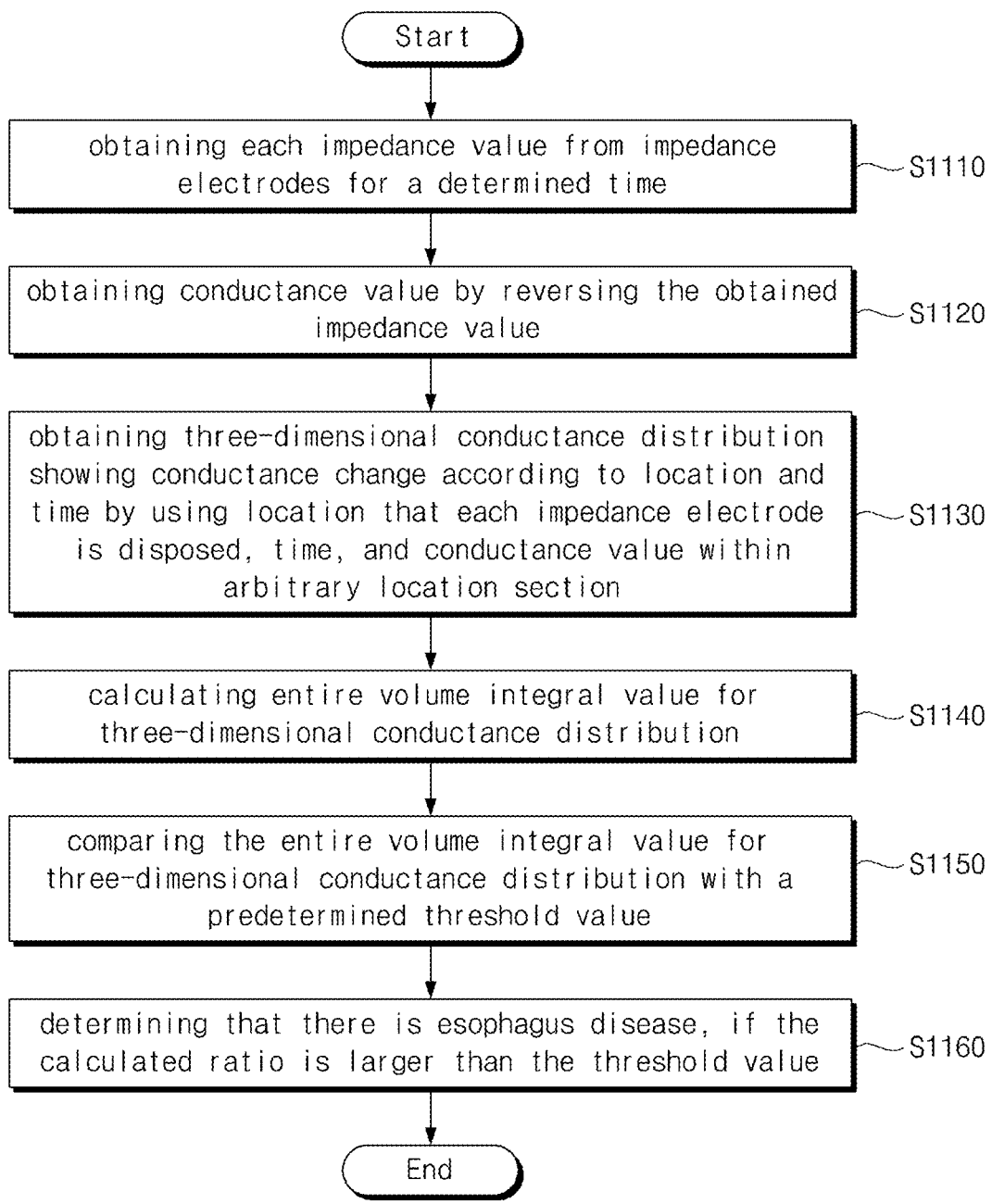

【Figure 12】
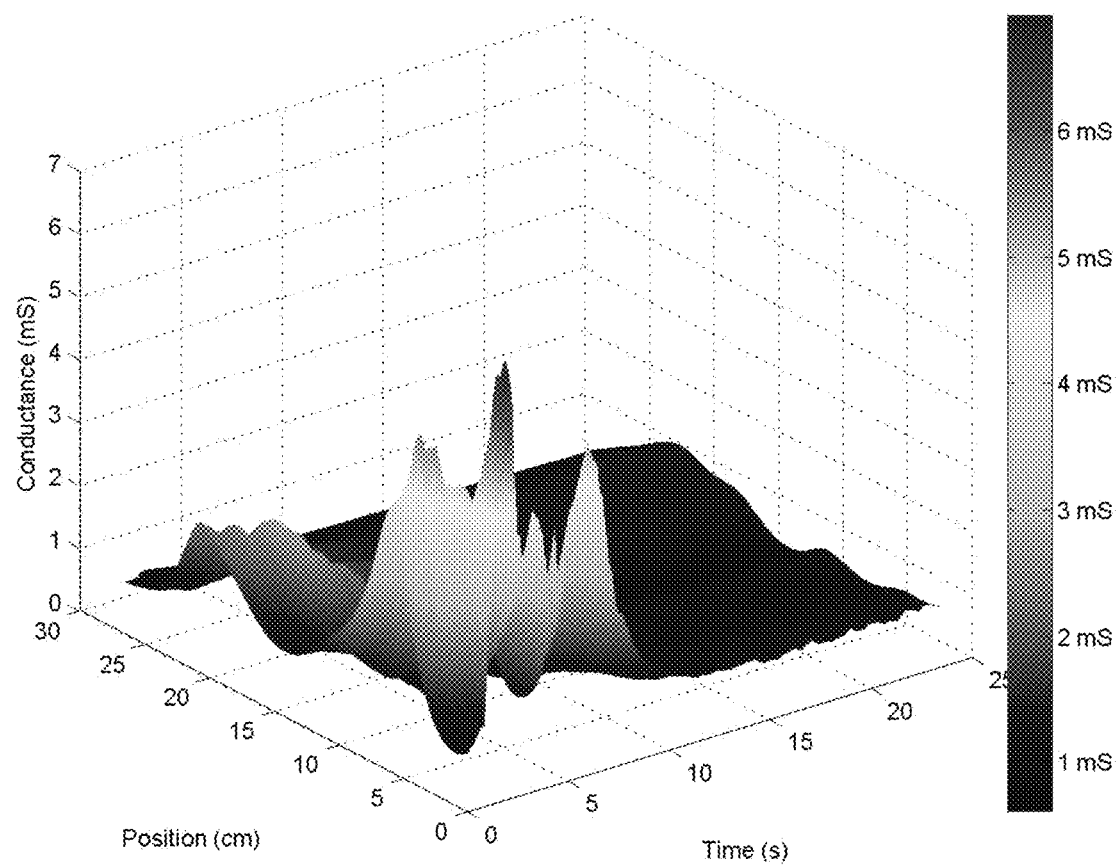

METHOD FOR DETECTING DISEASE USING HIGH RESOLUTION MANOMETRY, AND APPARATUS THEREOF

CROSS REFERENCE TO PRIOR APPLICATIONS

This application is a National Stage Application of PCT International Patent Application No. PCT/KR2015/002761 filed on Mar. 20, 2015, under 35 U.S.C. § 371, which claims priority to Korean Patent Application Nos. 10-2014-0033402 filed on Mar. 21, 2014 and 10-2014-0033403 filed on Mar. 21, 2014, which are all hereby incorporated by reference in their entirety.

TECHNICAL FIELD

The present invention relates to a method for detecting disease using a high resolution manometry, and an apparatus thereof. More particularly, the present invention relates to a method for detecting disease using a high resolution manometry, and an apparatus thereof that uses high resolution manometry having a plurality of pressure sensor or a plurality of impedance electrodes to examine anus rectum disease or esophagus disease.

BACKGROUND ART

Rectum and anus performs important physiological function for normal defecation. Due to the function abnormality of rectum and anus, a patient complains of constipation, stool residual feeling, fecal incontinence, and so on.

The methods for verifying the function abnormality of rectum and anus includes colonoscopy, balloon expulsion test, defecography, anus sphincter electromyography, anorectal manometry, and so on. Most represent method testing the function of rectum and anus among them is a anorectal manometry, which is mainly applied to anus sphincter function test and treatment planning for a defecation disorder patient or a perioperative patient of rectum anus area.

A anorectal manometry inserts manometry, which a plurality of pressure sensors are disposed, into anus and obtain pressure value, and determines disease by using the obtained pressure value. In general, a representative value among all sensor values in a manometry is used, or an average value is used, and there is a drawback that an accuracy and reliability of disease determination is deteriorated.

Also, esophagus disease shows aphagopraxia, ptyalorrhea, nausea, and so on, and it is necessary to test esophagus to verify the disease. In case of esophagus movement disease causing aphagopraxia, it is difficult to verify this through upper endoscopy, and it is necessary to perform esophagus internal pressure test, that is to say manometry test. These manometry test is performed by sensors that are arranged at intervals of 5 centimeters in the seventies or eighties to analyze the result value, but a high resolution manometry has been developed in the last decade, in which sensors are arranged at intervals of 1 centimeter dense than that of the conventional art to verify disease.

An impedance test method that is limitedly used to verify a gastroesophageal reflux disease is noticed by an idea that amount of bolus swallowed through esophagus is detected by indirect resistance, and it is attached to a high resolution manometry catheter to be used.

In this connection, a catheter in which a plurality of impedance electrodes are formed in a length direction is inserted into a esophagus in a high resolution impedance manometry, characteristics of bolus is detected based on resistance change, and esophagus disease can be verified by these results. If the amount of transit object in esophagus remains more, the impedance value is lowered, and therefore possibility of esophagus disease is increased.

However, an impedance test method using the high resolution manometry catheter has many limitations in analyzing the result value, decisively does not show accurate objective number, and there was a limitation in a clinical use.

As a back ground art of the present invention, there is a KOREA Patent No. 0816847 (published in 2008.03.19) and Patent Laid-Open Publication No. 2002-0093860(Dec. 16, 2002).

The above information disclosed in this Background section is only for enhancement of understanding of the background of the invention and therefore it may contain information that does not form the prior art that is already known in this country to a person of ordinary skill in the art.

DISCLOSURE

Technical Problem

The present invention has been made in an effort to provide a method for detecting disease using a high resolution manometry, and an apparatus thereof having advantages of improving determination efficiency of each disease related to rectum anus or esophagus.

Technical Solution

The present invention provides a method for detecting disease using a manometry according to the present invention includes obtaining pressure values from each of the plurality of pressure sensors during a pre-set time, obtaining a three-dimensional pressure distribution showing the changes in the pressure values according to location and time by using the time, the pressure values, and locations in which the pressure sensors are disposed within the arbitrary location section, and calculating the volume integral value of the interest location which is predetermined in accordance with the disease, in the three-dimensional pressure distribution.

Wherein the arbitrary location section includes a first section corresponding to a rectum area and a second section corresponding to an anus area when the manometry is inserted, and in the calculating the volume integral value, when the disease is constipation, the first section is set to the interest location to calculate the volume integral value and when the disease is fecal incontinence, the second section is set to the interest location to calculate the volume integral value.

Also, the method for detecting anus diseases using a manometry in a case that the disease is constipation may further include calculating a ratio of a volume integral value of the first section to the entire volume integral value of the three-dimensional pressure distribution, comparing the calculated ratio with a predetermined threshold value, and determining that there is constipation disease, if the calculated ratio is less than the threshold value.

Also, the method for detecting anus diseases using a manometry in a case that the disease is fecal incontinence may further include comparing a volume integral value of the second section with a predetermined threshold value, and determining that there is fecal incontinence disease, if the volume integral value of the second section is less than the threshold value.

Also, the method for detecting anus diseases using a manometry may further include dividing the arbitrary location section to a first section and a second section within the arbitrary location section according to the predetermined ratio, if the ratio of the first section and the second section is predetermined, and setting an interest section among the first section and the second section.

And, this invention provides an apparatus for detecting anus diseases using a manometry that a plurality of pressure sensors are disposed at determined intervals along an arbitrary location section in a length direction that includes a pressure value obtaining portion that obtaining pressure values from each of the plurality of pressure sensors during a pre-set time, a three-dimensional distribution obtaining portion that obtains a three-dimensional pressure distribution showing the changes in the pressure values according to location and time by using the time, pressure values, and locations in which the pressure sensors are disposed within the arbitrary location section, and a volume integral calculation portion that calculates the volume integral value of the interest location which is predetermined in accordance with the disease, in the three-dimensional pressure distribution Wherein the arbitrary location section includes a first section corresponding to a rectum area and a second section corresponding to an anus area when the manometry is inserted, and the volume integral calculation portion sets the first section to the interest location section to calculate the volume integral value, when the disease is constipation and sets the second section to the interest location to calculate the volume integral value, when the disease is fecal incontinence.

Also, the apparatus for detecting anus diseases using a manometry in a case that the disease is constipation, may further include a ratio calculation portion that calculates a ratio of a volume integral value of the first section to the entire volume integral value of the three-dimensional pressure distribution, a threshold value comparing portion that compares the calculated ratio with a predetermined threshold value, and a disease determination portion that determines that there is constipation disease, if the calculated ratio is less than the threshold value.

Also, the apparatus for detecting anus diseases using a manometry in a case that the disease is fecal incontinence, may further include a threshold value comparing portion that compares a volume integral value of the second section with a predetermined threshold value, and a disease determination portion that determines that there is fecal incontinence disease, if the volume integral value of the second section is less than the threshold value.

Also, the apparatus for detecting anus diseases using a manometry may further include a section dividing portion that divides the arbitrary location section to a first section and a second section within the arbitrary location section according to the predetermined ratio, if the ratio of the first section and the second section is predetermined, and an interest section setting portion that sets an interest section among the first section and the second section.

And, the present invention provides a method for detecting esophagus disease using high resolution esophagus impedance manometry that a plurality of impedance electrodes are disposed at predetermined intervals along an arbitrary location section of a length direction that include obtaining each impedance value from the plurality of impedance electrodes for a predetermined time, obtaining conductance value by reversing the obtained impedance value, obtaining three-dimensional conductance distribution showing conductance change according to location and time by using the time, the conductance value, and locations that each impedance electrode is disposed within the arbitrary location section, and calculating entire volume integral value for the three-dimensional conductance distribution.

Wherein, the method for detecting esophagus disease using high resolution esophagus impedance manometry may further include comparing entire volume integral value for the three-dimensional conductance distribution with a predetermined threshold value, and determining that there is esophagus disease, if the calculated ratio is larger than the threshold value.

Also, the calculating entire volume integral value calculates volume integral value of a predetermined interest location section within the three-dimensional conductance distribution in a case that a patient has a disorder in a esophagus, and the interest location section is a section corresponding to a normal esophagus area not having disorder among the arbitrary location sections when the high resolution esophagus impedance manometry is inserted.

Also, the method for detecting esophagus disease using high resolution esophagus impedance manometry may further include setting the interest location section within the arbitrary location section.

And, this invention provide an apparatus for detecting esophagus disease using high resolution esophagus impedance manometry that a plurality of impedance electrodes are disposed at predetermined intervals along an arbitrary location section of a length direction that includes an impedance obtaining portion that obtains each impedance value from the plurality of impedance electrodes for a predetermined time, a conductance obtaining portion that obtains conductance value by reversing the obtained impedance value, a three-dimensional distribution obtaining portion that obtains three-dimensional conductance distribution showing conductance change according to location and time by using the time, the conductance value, and locations that each impedance electrode is disposed within the arbitrary location section, and a volume integral calculation portion that calculates entire volume integral value for the three-dimensional conductance distribution.

Wherein the apparatus for detecting esophagus disease using high resolution esophagus impedance manometry may further include a threshold value comparing portion that compares entire volume integral value for the three-dimensional conductance distribution with a predetermined threshold value, and a disease determination portion that determining that there is esophagus disease, if the calculated ratio is larger than the threshold value.

Also, the volume integral calculation portion calculates volume integral value of a predetermined interest location section within the three-dimensional conductance distribution in a case that a patient has a disorder in a esophagus, and the interest location section is a section corresponding to a normal esophagus area not having disorder among the arbitrary location sections when the high resolution esophagus impedance manometry is inserted.

Also, the apparatus for detecting esophagus disease using high resolution esophagus impedance manometry may further include an interest section setting portion that sets the interest location section within the arbitrary location section.

Advantageous Effects

According to a method for detecting disease using a high resolution manometry, and an apparatus thereof of the present invention, pressure values of partial sensor related to rectum or anus area are used among a plurality of sensors provided in the manometry during the insertion of a manometry to be able to enhance determination efficiency of each disease related to rectum anus.

Also, according to the present invention, an inverse number of impedance of a plurality of impedance electrodes provided in a high resolution esophagus impedance manometry is used to obtain space-time three-dimensional distribution of conductance, and these are used to be able to improve esophagus disease determination efficiency.

DESCRIPTION OF THE DRAWINGS

FIG. 1 shows a manometry used in a first exemplary embodiment of the present invention.

FIG. 2 is a schematic diagram of anus disease detection apparatus using a manometry according to a first exemplary embodiment of the present invention.

FIG. 3 is a flowchart of an anus disease detection method using the apparatus of FIG. 2.

FIG. 4 shows a three-dimensional pressure distribution obtained in the S320 of FIG. 3.

FIG. 5 is a flowchart showing a method for detecting constipation disease after the S330 of FIG. 3.

FIG. 6 is a flowchart showing a method for detecting fecal incontinence disease after S330 of FIG. 3.

FIG. 7 shows a classification embodiment of a first section and a second section in a first exemplary embodiment of the present invention.

FIG. 8 shows an exemplary embodiment high resolution esophagus impedance manometry used in a second exemplary embodiment of the present invention.

FIG. 9 shows an image that saline is injected through esophagus in FIG. 8.

FIG. 10 is a schematic diagram of a esophagus disease detection apparatus using high resolution esophagus impedance manometry according to a second exemplary embodiment of the present invention.

FIG. 11 is a flowchart of a method for detecting a esophagus disease using the apparatus of FIG. 10.

FIG. 12 shows three-dimensional conductance distribution obtained from S1130 of FIG. 11.

MODE FOR INVENTION

The present invention will be described more fully hereinafter with reference to the accompanying drawings, in which exemplary embodiments of the invention are shown.

The present invention relates to a method for detecting disease using a high resolution manometry, and an apparatus thereof. The present invention is divided to main two exemplary embodiments. Firstly, a first exemplary embodiment of the present invention provides an anus rectum disease detection method using high resolution anus rectum manometry and the apparatus thereof. And, a second exemplary embodiment of the present invention provides a esophagus disease detection method high resolution esophagus manometry and the apparatus thereof.

Hereinafter, firstly a first exemplary embodiment of the present invention will be described in detail.

A first exemplary embodiment of the present invention relates to an anus rectum disease detection method using a high resolution anus rectum manometry, a manometry that a plurality of pressure sensors is disposed at a predetermined interval along a length direction is used to detect an internal pressure of anus or rectum area, the detected value is used to detect the disease such as constipation or fecal incontinence.

Generally, a manometry is a device that is used for detecting internal pressure of rectum and anus, and various types thereof are well known to. FIG. 1 shows a manometry used in a first exemplary embodiment of the present invention. Here, a first exemplary embodiment of the present invention is not limited to a manometry shape of FIG. 1.

Referring to FIG. 1, a manometry 10 includes a plurality of pressure sensors that are disposed at predetermined intervals along arbitrary location section of the length direction thereof (in case of FIG. 1, 1 centimeter interval along 1.0-6.0 cm section). In FIG. 1, the arbitrary location section are divided into 5 sections at an interval of 1 centimeter, a plurality of pressure sensors is disposed at each section (Referring to Anal Canal Radial Sensors part of FIG. 1).

As shown in FIG. 1, in a case that a plurality of sensors is disposed in radial direction at each section, pressure value of each sensor is processed by an arbitrary method (ex, average calculation), and the processed value may be an representative value for the related section. The mounting number of the pressure sensor for each section may be varied by considering importance of the section, sensor error, and accuracy rate.

In addition to the pressure sensors for detecting the internal pressure, a manometry 10 may include configurations such as Intra-balloon Pressure Sensor, Anal Verge Position Band, Rectal Pressure Sensor, and External Reference Channel as shown in FIG. 1, and the detail description thereof will be omitted.

In a first exemplary embodiment of the present invention, the sensor corresponding to the rectum area among entire sensors may be used to verify constipation disease, and the sensor corresponding to the anus area may be used to verify fecal incontinence disease. As shown in FIG. 1, upper most one section among five sections may be used to verify constipation disease, and the rest four sections may be used to verify fecal incontinence disease. Of course, the ratio that the section is divided is not limited to 1:4 of FIG. 1. The ratio may be varied depending on the condition such as sex, age, height, and organ length of an examinee.

Hereinafter, a method for detecting anus disease using a manometry and the apparatus thereof according to first exemplary embodiment of the present invention will be described in detail. Just, for better comprehension and ease of description, one exemplary embodiment that one pressure sensor is disposed at each divided section is described.

FIG. 2 is a schematic diagram of anus disease test apparatus using a manometry according to a first exemplary embodiment of the present invention, and FIG. 3 is a flowchart of an anus disease detection method using the apparatus of FIG. 2.

Referring to FIG. 2 and FIG. 3, an anus disease detection apparatus 100 according to a first exemplary embodiment of the present invention includes a pressure value obtaining portion 110, a three-dimensional distribution obtaining portion 120, a volume integral calculation portion 130, a ratio calculation portion 140, a threshold value comparing portion 150, a disease determination portion 160, a section dividing portion 170, and an interest section setting portion 180.

Firstly, a pressure value obtaining portion 110 obtains each pressure value from a plurality of pressure sensor of a manometry 10 for a predetermined time S310. As shown in FIG. 1, a plurality of pressure sensor is disposed on arbitrary location section (ex, 1.0-6.0 cm section) along the length direction of the manometry 10 at a predetermined interval (ex, 1 centimeter interval).

The S310 obtains pressure values from the pressure sensors those are disposed on the divided five sections, and this is continued for a predetermined time. Then, sensing value change of each pressure sensor may be obtained as time passes, and sensing value change may be obtained depending on the location of each pressure sensor, (mounting location in the manometry)

After this, a three-dimensional distribution obtaining portion 120 uses location that each pressure sensor is disposed within the arbitrary location section, time, and the obtained pressure value to obtain three-dimensional pressure distribution that shows the changes of the pressure values according to the location and the time S320.

FIG. 4 shows a three-dimensional pressure distribution obtained in the S320 of FIG. 3. X axis of FIG. 4 denotes time (s), Y axis denotes mounting location of sensor (cm), and Z axis denotes pressure value (mmHg).

FIG. 4 shows pressure data obtained for 10 seconds. Y axis showing mounting locations of sensors is drawn from 0 to 5 centimeters for the convenience of diagram, and this corresponds to the location ranging from 1 to 6 centimeters that each sensor is located in FIG. 1. This three-dimensional pressure distribution has surface shape having a three-dimensional effect.

Meanwhile, each pressure sensor is disposed at an interval of 1 centimeter along the length direction of the manometry 10 (Y axis direction) in a first exemplary embodiment of the present invention, and therefore pressure value between the sections (that the sensor is not mounted) cannot be obtained. However, if a curved line smooth method is used by connecting each point location, continuous data may be obtained between the sections as shown in FIG. 4. Surely, this method may be applied to the pressure values (X axis direction) according to time. Like this, the sensing points are connected by curved line or curbed surface, and the method that obtains middle values between each point that is well known as a conventional art may be used.

In a first exemplary embodiment of the present invention, data of FIG. 4 is used to perform volume integral for the arbitrary interest section so as to verify various diseases. That is, a volume integral calculation portion 130 calculates volume integral value within the three-dimensional pressure distribution for a predetermined interest location section corresponding to the disease S330.

In a first exemplary embodiment of the present invention, the arbitrary location section includes a first section corresponding to rectum area (an upper section among five sections in FIG. 1) and a second section corresponding to anus area (remaining lower sections in FIG. 1) while the manometry 10 is being inserted. An upper section and lower sections are shown by different shadow of hatching.

On the premises, the volume integral calculation portion 130 sets the first section (an upper section) to the interest location section to calculate volume integral value in a case that the disease is constipation, and sets the second section (lower sections) to the interest location section to calculate volume integral value in a case that the disease is fecal incontinence.

For example, if a constipation disease test is selected by an user, a first section (an upper section) is set to an interest location section, and if fecal incontinence disease test is selected by an user, second sections (lower sections) are set to an interest location section to calculate volume integral value. An apparatus according to a first exemplary embodiment of the present invention further include an input portion for setting of a user.

Based on the above description, hereinafter, a detailed examination method will be described for constipation disease using a first section. FIG. 5 is a flowchart showing a method for detecting constipation disease after the S330 of FIG. 3.

First, a ratio calculation portion 140 calculates a ratio of a volume integral value of the first section (upper section) to an entire volume integral value of the three-dimensional pressure distribution in a case that the examination disease is constipation S510. For example, an entire volume integral value (A) is calculated for three-dimensional pressure distribution of FIG. 4, a volume integral value (A') is calculated based on the data ranging from 4 to 5 centimeters (first section; upper section) from the entire three-dimensional pressure distribution of FIG. 4, and A' is divided by A to calculate a ratio.

Then, a threshold value comparing portion 150 compares the calculated ratio to a predetermined first threshold value S520. Here, in the S510, if the calculated ratio is larger than the first threshold value, it is determined to a normal condition, and if it is less than the first threshold value, it is determined that there is constipation disease S530.

Next, an examination method using a second section for fecal incontinence will be described in detail. FIG. 6 is a flowchart showing a method for detecting fecal incontinence disease after S330 of FIG. 3. In this process, a ratio value that is described above is not used, and absolute value of volume integral for the related area is used.

Like this, in a case that an examination disease is fecal incontinence, a volume integral calculation portion 130 calculates volume integral value of a second section (lower section) in S330.

After this, as shown in FIG. 6, a threshold value comparing portion 150 a volume integral value of a second section (a lower section) with a predetermined second threshold value S610. And then, a disease determination portion 160 determines that a patient don't have disease, if the volume integral value of the second section is larger than the second threshold value, and determines that a patient have fecal incontinence disease, if it is less than a second threshold value S620.

Here, the first section (upper section) and the second section (lower section) may be varied depending on the body structure of the patient. Two sections may be finally set depending on the body condition of the patient. The disease determination accuracy and reliability may be further enhanced through this process.

For this purpose, a first exemplary embodiment of the present invention includes a section dividing portion 170 and an interest section setting portion 180. If the section dividing portion 170 receives the set ratio between the first section and the second section within the arbitrary location section to divide the arbitrary location section to a first section (upper section) and a second section (lower section) depending on the set ratio.

For example, the ratio of 1:4 is set by an user, a first section and a second section are automatically divided as shown in FIG. 1, and they are separated by color or hatching. Also, in a case that the five sections are formed according to the location of the pressure sensor in FIG. 1, a menu may be provided on a display screen to receive one ratio among ratios of 1:4, 2:3, 3:2, and 4:1.

After this, an interest section setting portion 180 sets the interest location section from the first section (upper section) and the second section (lower section). That is, if constipation disease is suspected, a first section is set to an interest location section, and a method of FIG. 5 may be used after the process of FIG. 3. Also, if fecal incontinence disease is suspected, a second section is set to an interest location section, and a method of FIG. 6 is used after the method of FIG. 3. Like this, a section division or a setting of an interest location section may be performed before S310 of FIG. 3. Of course, this process may be performed by any steps before S330.

FIG. 7 shows a classification embodiment of a first section and a second section in a first exemplary embodiment of the present invention. A, B, C, and D of FIG. 7 shows embodiments that the ratios between the first section and the second section may be set to 1:4, 2:3, 3:2, and 4:1.

As described above, in a method for detecting disease using a manometry and the apparatus thereof according to a first exemplary embodiment of the present invention, pressure values of the related sensors that are related to rectum or anus area among a plurality of sensors that are disposed in the manometry are used to verify various disease related to rectum anus, and the determination efficiency is enhanced while the manometry is inserted.

Also, three-dimensional volume distribution that pressure values of each sensor is processed in time and space is used according to a first exemplary embodiment of the present invention, different from that a simple pressure value is used in a conventional anorectal manometry, such that this process may suggest new method that may verify functional colon anus movement disease.

Hereinafter, a second exemplary embodiment of the present invention will be described in detail.

A second exemplary embodiment of the present invention relates to a esophagus disease detection method and the apparatus thereof using a high resolution esophagus impedance manometry, and a detection value of a high resolution esophagus impedance manometry that a plurality of impedance electrodes are disposed along the length direction at a predetermined interval is used to verify the disease within esophagus.

FIG. 8 shows an exemplary embodiment high resolution esophagus impedance manometry used in a second exemplary embodiment of the present invention. Here, a second exemplary embodiment of the present invention is not limited to the condition of FIG. 8.

Referring to FIG. 8, a high resolution esophagus impedance manometry 20 includes a plurality of impedance electrode (Z1-Z16) those are disposed along arbitrary location section of the length direction at a predetermined interval (2 centimeters interval in FIG. 8). More specifically, impedance electrodes (ex, 16 things) those are arranged at 2 centimeters interval are disposed between a plurality of pressure sensors (ex, 36 things) those are arranged at 1 centimeter interval to detect pressure to be configured to a catheter having a finger thickness. In this high resolution esophagus impedance manometry 20, after a catheter is inserted into a nostril, a patient swallows saline about ten times for about 5 to 10 minutes and thereby all test ends.

A second exemplary embodiment of the present invention may provide a method that may show objective value from the values detected from the impedance sensors those are arranged at 2 centimeters interval on the high resolution impedance manometry, and this method is based on the theory that the esophagus movement has a problem, if the swallowed bolus cannot get out of the esophagus within a predetermined time to remain in the esophagus.

A high resolution esophagus impedance manometry shown in FIG. 8 is well known to a person in the skilled in this art, and the detailed description will be omitted. Of course, a second exemplary embodiment of the present invention is not limited to the configuration of the manometry shown in FIG. 8.

FIG. 9 shows an image that saline is injected through esophagus in FIG. 8. A esophagus impedance test is a method that detects properties of transit object (ex, saline) based on the resistance variation. If the amount of saline that is remained in the esophagus is larger after the saline is injected, the impedance is deteriorated and the conductivity is increased.

Hereinafter, a second exemplary embodiment of the present invention will described a esophagus disease detection method and the apparatus using a high resolution esophagus impedance manometry.

FIG. 10 is a schematic diagram of a esophagus disease detection apparatus using high resolution esophagus impedance manometry according to a second exemplary embodiment of the present invention, and FIG. 11 is a flowchart of a method for detecting a esophagus disease using the apparatus of FIG. 10.

Referring to FIG. 10 and FIG. 11, a esophagus disease detection apparatus 200 according to a second exemplary embodiment of the present invention includes an impedance obtaining portion 210, a conductance obtaining portion 220, a three-dimensional distribution obtaining portion 230, a volume integral calculation portion 240, a threshold value comparing portion 250, a disease determination portion 260, a section dividing portion 270, and an interest section setting portion 280.

Firstly, an impedance obtaining portion 210 obtains each impedance value from a plurality of impedance electrodes provided in the impedance manometry 20 for a predetermined time S1110.

As shown in FIG. 8, a plurality of impedance electrodes are disposed along arbitrary location section in the length direction of the impedance manometry 20 at a predetermined interval (ex, 2 centimeters interval). Here, it is obvious that the arbitrary location section denotes a partial of the entire length of a pipe portion of the impedance manometry 20.

The S1110 step obtains impedance value from each impedance electrode, and this is continued for a predetermined time. Then, change property of the impedance value in each impedance electrode may be obtained according to time, and change property of the impedance value may be obtained according to the location of the impedance electrode (mounting location in the impedance manometry 20).

After this, a conductance obtaining portion 220 reverse the obtained impedance value to calculate the conductance value S1120. The S1120 step denotes that all impedance values obtained in the previous S1110 step is reversed to be changed to the conductance value.

Next, a three-dimensional distribution obtaining portion 230 uses location that each impedance electrode is disposed within arbitrary location section that the electrode is disposed, the time, and the conductance value and obtains three-dimensional conductance distribution that denotes conductance change according to the location and time S1130.

FIG. 12 shows three-dimensional conductance distribution obtained from S1130 of FIG. 11. In the FIG. 12, X axis denotes time (s), Y axis denotes mounting locations of electrodes (cm), and Z axis denotes conductance value (mS).

FIG. 12 shows the data of the conductance value for 25 seconds. Y axis that shows the mounting location of the impedance electrode ranges from 0 to 30 centimeters. The three-dimensional conductance distribution has a surface shape having one three-dimensional shape.

Meanwhile, in a second exemplary embodiment of the present invention, because each impedance electrode is disposed along the length direction (Y axis direction) of the impedance manometry 20 at an interval of 2 centimeters, the conductance value between them cannot be obtained in detail. However, if a curved line method is used to connect each point location, continuous data may be obtained between each point as shown in FIG. 12.

Of course, this method may be equally applied to conductance values (X axis direction) according to time. Like this, a method that the calculated each points are connected to form a curved line and a curved surface can use a method that is well known to a person skilled in this art.

In a second exemplary embodiment of the present invention, data of FIG. 12 is used to verify esophagus disease. That is, a volume integral calculation portion 240 calculates entire volume integral value for the three-dimensional conductance distribution S1140. For example, volume integral value of entire three-dimensional conductance distribution that is obtained from the section ranging from 0 to 30 centimeters for 25 seconds is calculated as shown in FIG. 12.

In that order, a threshold value comparing portion 250 compares the entire volume integral value for the three-dimensional conductance distribution with a predetermined threshold value S1150. Next, a disease determination portion 260 determines that a patient has the esophagus disease, if the calculate ratio is larger than the threshold value S1160.

A conductance is a concept that is in opposition to impedance, if the impedance is low, the possibility of the disease is increased, and therefore if the conductance value is high, the possibility of the disease is high.

Here, in a case that a patient has a possibility to have a esophagus disorder, the entire of the three-dimensional conductance distribution is not used and a partial section (ex, 10 to 20 centimeters) is used. That is, in the S1140 step, volume integral value of a predetermined interest location section is calculated within the three-dimensional conductance distribution in a case that a patient has a esophagus disorder. That is, the volume integral value of the partial section is compared to a threshold value so as to verify the disease possibility. The threshold value that is used in this process may be less than a threshold value that is used for the entire section. That is, the threshold value may be varied in proportion to ratio of a partial length section to the entire electrode length section.

Here, the interest location section may denotes a section that corresponds to normal esophagus area not having esophagus disorder among sections that electrodes, when the impedance manometry 20 are disposed is inserted into esophagus. That is, in a case that a patient has a partial disorder in esophagus function, the section not having function disorder is used to determine whether the esophagus is normal or abnormal, and has lesion or not.

Here, in a second exemplary embodiment of the present invention, because the area having normal function is different depending on examinee (or patient), a function that may set an interest section is included. That is, an interest section setting portion 280 may set the interest location section within the section (0 to 30 centimeters) that the impedance electrodes are disposed in the impedance manometry 20. A process that sets the interest location section may be performed before S110 step of FIG. 11. Surly, the setting process may be performed by any steps before S1140 step.

As described above, a second exemplary embodiment of the present invention uses an inverse number of impedance of a plurality of impedance electrodes provided in a high resolution esophagus impedance manometry to obtain space-time three-dimensional distribution of conductance, and these are used to be able to improve esophagus disease determination efficiency.

Also, according to a second exemplary embodiment of the present invention, differently from that an impedance value is simply compared to a standard value in a conventional impedance test, three-dimensional conductance distribution that a conductance value that an impedance value of each electrode is reversed is processed in time and space is used, and a new esophagus disease detection method that three-dimensional integral volume according to time and space is used may be introduced.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A method for detecting anus diseases using a manometry that a plurality of pressure sensors are disposed at determined intervals along an arbitrary location section in a length direction, comprising;
  obtaining pressure values from each of the plurality of pressure sensors during a predetermined time;
  obtaining a three-dimensional pressure distribution showing the changes of the pressure values according to location and time by using the time, the pressure values, and locations in which the pressure sensors are disposed within the arbitrary location section; and
  calculating the volume integral value of the interest location which is predetermined in accordance with the disease within the three-dimensional pressure distribution.

2. The method for detecting anus diseases using a manometry of claim 1, wherein the arbitrary location section includes a first section corresponding to a rectum area and a second section corresponding to an anus area while the manometry is inserted, and
  in the calculating the volume integral value, in a case that the disease is constipation, the first section is set to the interest location to calculate the volume integral value and in a case that the disease is fecal incontinence, the second section is set to the interest location to calculate the volume integral value.

3. The method for detecting anus diseases using a manometry of claim 2, further comprising;
  calculating a ratio of a volume integral value of the first section to the entire volume integral value of the three-dimensional pressure distribution;
  comparing the calculated ratio with a predetermined threshold value; and
  determining that there is constipation disease, if the calculated ratio is less than the threshold value.

4. The method for detecting anus diseases using a manometry of claim 2, further comprising;
  comparing a volume integral value of the second section with a predetermined threshold value; and
  determining that there is fecal incontinence disease, if the volume integral value of the second section is less than the threshold value.

5. The method for detecting anus diseases using a manometry of claim 2,
  further comprising;
  dividing the arbitrary location section to a first section and a second section within the arbitrary location section according to the predetermined ratio, if the ratio of the first section and the second section is predetermined; and setting an interest section among the first section and the second section.

\* \* \* \* \*